(12) United States Patent
Gisser et al.

(10) Patent No.: US 10,370,544 B2
(45) Date of Patent: *Aug. 6, 2019

(54) HIGH QUALITY BIOCIDAL PAINT

(71) Applicant: THE SHERWIN-WILLIAMS COMPANY, Cleveland, OH (US)

(72) Inventors: Kathleen R Gisser, Solon, OH (US); Morgan S Sibbald, Copley, OH (US); Wanda J Smith, Macedonia, OH (US); Janice K. Dreshar, Westlake, OH (US); Donald A. Prochazka, Strongsville, OH (US); Tony A. Rook, Lakewood, OH (US)

(73) Assignee: THE SHERWIN-WILLIAMS COMPANY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,658

(22) Filed: Jul. 5, 2016

(65) Prior Publication Data

US 2017/0086455 A1 Mar. 30, 2017

Related U.S. Application Data

(63) Continuation-in-part of application No. 15/071,385, filed on Mar. 16, 2016, and a continuation of application No. 14/823,123, filed on Aug. 11, 2015, and a continuation of application No. 13/552,966, filed on Jul. 19, 2012, now Pat. No. 9,131,683.

(60) Provisional application No. 61/541,168, filed on Sep. 30, 2011.

(51) Int. Cl.
| | |
|---|---|
| *C08K 5/17* | (2006.01) |
| *C09D 5/14* | (2006.01) |
| *C09D 5/16* | (2006.01) |
| *A01N 25/04* | (2006.01) |
| *A01N 25/10* | (2006.01) |
| *A01N 33/12* | (2006.01) |
| *A01N 43/40* | (2006.01) |
| *A61K 31/14* | (2006.01) |
| *C09D 133/08* | (2006.01) |
| *A61K 31/4425* | (2006.01) |

(52) U.S. Cl.
CPC ........... *C09D 5/1625* (2013.01); *A01N 33/12* (2013.01); *A01N 43/40* (2013.01); *A61K 31/14* (2013.01); *A61K 31/4425* (2013.01); *C08K 5/17* (2013.01); *C09D 5/14* (2013.01); *C09D 133/08* (2013.01); *Y02A 50/473* (2018.01)

(58) Field of Classification Search
CPC .................................. C09D 5/14; A01N 33/12
See application file for complete search history.

(56) References Cited

U.S. PATENT DOCUMENTS

| | | | | | |
|---|---|---|---|---|---|
| 4,018,611 | A | * | 4/1977 | Cramer | D06M 16/00 106/18.32 |
| 5,314,719 | A | * | 5/1994 | Batdorf | C09D 5/14 106/15.05 |
| 5,403,393 | A | * | 4/1995 | Dubble | C09D 5/024 106/277 |
| 6,238,732 | B1 | * | 5/2001 | Cameron | C08J 3/124 427/208.2 |
| 2004/0219128 | A1 | * | 11/2004 | Batdorf | A01N 25/10 424/78.27 |

OTHER PUBLICATIONS

Lonza (Bardac 205M, Bardac 208M Quaternary Ammonium Compounds. Lonza, Nov. 2007, 2 pages).*
Sherwin Williams (Coating Coverage Calculations. 2017, 1 page).*
Resene (Volume solids, PVC and hiding power. NZIA-Resene CPD. Aug. 2005, 14 pages).*
Accuratus (AOAC Method 961.02 Germidical Spray Method. Accuratus Lab Services. 2018, 1 page).*
Fuller (Fulatex PD0124 Technical Data Sheet. Universal Selector. 2016, 2 pages).*
Dow (Rovace 661 Vinyl-Acrylic Emulsion Technical Data Sheet. Dow. 2016, 4 pages).*

* cited by examiner

*Primary Examiner* — Brieann R Johnston
(74) *Attorney, Agent, or Firm* — Daniel S. Ward; James C Scott; Vivien Y. Tsang

(57) ABSTRACT

A high quality paint comprises water, latex polymer, pigment, and biocidal agent. The coating provided by the high quality paint may be capable of killing gram positive bacteria, gram negative bacteria at a rate of greater than 3 logs within 2 hours of application of bacteria to a painted surface. The coating provided by the high quality of paint may be capable of continuing to kill gram positive bacteria, gram negative bacteria at a rate of greater than 1 log within 2 hours even after repeated contamination of the surface. The coating provided by the high quality paint may be capable of delivering residual killing of gram positive bacteria, gram negative bacteria for up to 48 months. The coating provided by the high quality paint may also be capable of inactivating viruses.

15 Claims, No Drawings

HIGH QUALITY BIOCIDAL PAINT

This application is a continuation-in-part of U.S. patent application Ser. No. 15/071,385, filed on Mar. 16, 2016, which is a continuation of currently pending U.S. patent application Ser. No. 14/823,123, filed Aug. 11, 2015, which is a continuation of U.S. patent application Ser. No. 13/552,966, filed Jul. 19, 2012, now U.S. Pat. No. 9,131,683, which claims the benefit of U.S. Provisional Application No. 61/541,168, filed on Sep. 30, 2011, all hereby incorporated by reference.

This invention was made with Government support under Contract Number W911NF09C0025 awarded by the U.S. Army Research Office. The Government has certain rights in this invention.

FIELD OF THE DISCLOSURE

Disclosed is a high quality latex paint composition which contains a biocidal agent, in particular a quaternary ammonium compound.

BACKGROUND

Paints typically contain four essential ingredients: carrier liquid, binder, pigment, and additives. Each of such ingredients may comprise a single component or several different items mixed into the paint.

The carrier liquid is a fluid component of the paint which serves to carry all of the other components. The carrier liquid is part of the wet paint and usually evaporates as the paint dries to form a coating. In latex paints, the carrier liquid is usually water. In oil-based paints, the carrier liquid is usually an organic solvent. The amount and type of liquid is usually determined by features of the other paint components.

The binder component of a paint is what causes the paint to form a film on and adhere to a surface. In a latex paint, the binder comprises a latex resin, usually selected from acrylics, vinyl acrylics, or styrene acrylics. In a latex paint, the latex resin particles usually are in a dispersion with water as the carrier liquid.

Pigments provide the paint with both decorative and protective features. Pigments are solid particles used to provide the coating provided by the paint with various qualities, including but not limited to color, opacity, and durability.

In addition to pigments, the paint may also contain other solids such as polyurethane beads. Additionally, other components of wet paint may comprise a portion contributing to the solids of a paint. For instance, while the pigments are generally one-hundred percent solids, the binder and/or thickener may contain a portion contributing to the solids of the paint. The pigments and other solids add bulk to the paint and their levels are related to the gloss or flatness of the coating provided by dried films of the paint.

A multitude of additives may be included in paints. The additives are typically used at relatively low levels in the paint, but contribute to various properties, including rheology, stability, paint performance, and application quality.

Some biocides, specifically, antibacterial agents, are additives which have bacteriostatic and bactericidal properties. Some biocides work to kill bacteria by one or more of several different mechanisms, including but not limited to interfering with cell wall synthesis, damaging the cell membranes, inhibiting protein synthesis, and interfering with nucleic acid synthesis. Some biocides may also have anti-viral effects, serving to inactivate viruses, such as cold and flu viruses. Some biocides provide a bacteriostatic effect inhibiting reproduction of bacteria. Some biocide provide antimicrobial effects by killing or inhibiting the growth of microorganisms.

A variety of biocidal agents are well known and are used for various purposes. Such biocides include inorganic biocidal agents, for example, those containing metal ions, such as silver, zinc, and copper. Other inorganic biocides include phosphates, metal ion, metal or other biocide containing zeolites or hydroxyapatites. There are also organic biocides including organic acids, phenols, alcohols, and quaternary ammonium compounds.

Quaternary ammonium compounds act as biocides by damaging cell membranes and killing bacteria. This mechanism is likely due to the positive charge on the quaternary ammonium compounds which interact with the negative charge sites of the bacteria.

Quaternary ammonium compounds are not typically added to latex paints, due to a negative effect on the quality of the paint. The prior art has recognized that when added to latex paints, quaternary ammonium compounds cause an undesirable increase in viscosity and cause the polymer and pigments to precipitate. Without being limited to any particular theory, it is believed that the cationic nature of the quaternary ammonium compounds is not compatible with the generally anionic nature of latex paint which results in the precipitation of the components from the dispersion. The precipitation causes the paint to have an undesirable appearance as the precipitate particles cause the coating provided by the dry paint film to have a grainy appearance or texture.

DETAILED DESCRIPTION

A paint, in one embodiment, may comprise water, latex binder resin, pigment, and additives, wherein such additives include, but are not limited to, a biocidal agent. In some embodiments, the paint has one or more of the following characteristics: capability of providing a coating having a pigment volume concentration (PVC) of less than 60, about 25% to about 65% by weight solids, at least 17% by weight binder up to about 55% by weight binder polymer solids, at least 10% by weight of a hiding pigment, for example, titanium dioxide, and about 0.25% to about 3% by weight of at least one biocidal agent. In some embodiments the paint has from about 0.46% to about 0.58% biocidal agent by weight. In some embodiments the paint has from about 0.52 to about 0.56 biocidal agent by weight percentage. In some embodiments the biocidal agent is a quaternary ammonium compound.

A biocidal surface which is self-sustaining is desirable to consumers, as it fulfills a longstanding need. There is a long-standing need to provide a surface that has an effective rate of biocidal activity. For example, in an article that appeared in the American Journal of Infection Control (American Journal of Infection Control 42 (2014) 1178-1181) an argument was made for the need for a surface which could provide continuous disinfecting action and the researchers were able to show that the surface that they had prepared by treating with an organosilane quaternary ammonium formulation that is spray applied to a surface could provide a 2 log level of biocidal activity which lasted up to 15 weeks. The researchers recommended following such a treatment every 3-4 weeks. However, such a monthly treatment of a surface is not practical or cost-effective for institutional-type users who are in need of a biocidal surface. Further, it had been hypothesized by some in the art that the use of a quaternary ammonium compound is not an effective surface active agent because of its limited efficacy (http://www.micro-blog.info/2014/02/an-overview-of-the-options-for-antimicrobial-surfaces-in-hospitals/). Additionally, the application of a quaternary ammonium compound based liquid hard surface disinfectant may provide a limited amount of residual sanitizing ability if there is no interaction with the surface. Once the surface has been interacted with, whether to clean or simply by touch of a hand or article, the residual quaternary ammonium compound is easily removed and ceases to provide residual sanitizing activity. Accordingly, a biocidal surface which is self-sustaining is desirable.

Self-sustaining means that the surface (whether inherently, or through the use of a coating) provides biocidal effects and does not need any sort of "recharging" or replenishment. A self-sustaining surface will be more readily used by consumers than a surface that either only provides short-term biocidal effects or a surface that constantly needs to undergo re-treatment or have an active feedstream of active ingredient to it for it to maintain its biocidal effects. One effective way of measuring the efficacy at which a surface provides a self-sustaining biocidal effect is to calculate that surface's Rook Rating. The Rook Rating provides a relative comparison of initial efficacy of the biocidal activity of a surface and efficacy of the biocidal activity of the surface after some elapsed period of time.

Rook Rating$_{Time\ Period}$=Efficacy$_{Time\ Period}$/Efficacy$_{Initial}$

The Rook Rating may also provide a relative comparison of initial efficacy of the biocidal activity of a surface and efficacy of the biocidal activity of the surface after an event or series of event has occurred.

Rook Rating$_{Event}$=Efficacy$_{Event}$/Efficacy$_{Initial}$

Without wishing to be limited, it can be assumed that in a commercial context, walls or other surfaces, are coated about every four years. Thus, the Rook Rating with respect to a period of four years (forty-eight months), or a simulation of such period, may indicate whether a paint provides a coating with self-sustaining biocidal effect for a four year (forty-eight month) period of time.

As is described further, in spite of having a favorable compatibility score, adding too much quaternary ammonium compound is likely to cause the resultant paint to have an unacceptable level of precipitates or other inconsistencies in the texture of the coating provided by the dried paint film.

In some embodiments, the latex binder resin and the quaternary ammonium compound have a compatibility score of less than 0.7 g, for example, less than 0.5 g, and further for example, less than 0.35 g, as measured by the Polymer/Quaternary Ammonium Compound Compatibility Test (hereinafter "Compatibility Test") described herein. Some embodiments may comprise a high quality paint having broad spectrum biocidal capabilities. In some useful embodiments, the dried paint film of the paint provides a coating capable of reducing gram positive bacteria, gram negative bacteria, and viruses by greater than 3 logs within 2 hours of application of the bacteria or viruses to the coated surface. Embodiments may also comprise a surface having such a coating on at a least portion thereof. Bacterial and viral reduction is measured in a test based on the Japanese Industrial Standard (JIS) Z 2801 as described herein and compared to a control paint providing a coating on a surface that does not contain an identified biocidal agent.

The coating provided by application of the paint to a surface may have a dry coating thickness of from about 25 micron to about 400 microns. In some embodiments, the dry coating thickness is from about 50 microns to about 200 microns. In some embodiments, the dry coating thickness is from about 50 microns to about 100 microns.

Embodiments of the paint may comprise various components contributing to the total solid content of the paint, such as pigments and/or polyurethane beads. In some embodiments, a portion of the binder left behind when the paint dries to form a film may contribute to the total solid content. In some embodiment, a portion of the thickener left behind when the paint dries to form a film may contribute to the total solid content.

In some embodiments the paint comprises about 15 weight percent total solids and provides a dry coating thickness from about 5.7 microns to about 38.1 microns. In some embodiments, the paint comprises about 15 weight percent total solids and provides a dry coating thickness of about 9.9 microns to about 66 microns. In some embodiments, the paint comprises about 35 weight percent solids and provides a dry coating thickness of about 35.5 microns to about 101.6 microns. In some embodiments, the paint comprises about 55 weight percent total solids and provides a dry coating thickness of about 167.6 microns to about 304.8 microns. In some embodiments the paint comprises about 55 weight percent total solids and provides a dry coating thickness of about 698.5 microns to about 1270 microns.

In some embodiments, a paint providing a self-sustaining coating is applied in a single application (i.e., applied as a paint coating would be applied by one of skill in the art). In some embodiments, a paint providing a self-sustaining coating is applied in two applications. In some embodiments still, a paint providing a self-sustaining coating is applied in three or more applications.

In some embodiments, the paint may be applied by either a brush or by roller.

In some embodiments, the paint may be applied by spray application. In some embodiments still, the paint is applied to a surface which has had a primer applied to that surface first.

In some embodiments, the pigments used in the paint have a minimum fineness of grind by Hegman gauge of at least 4, for example, at least 5. Further, the paint may have one or more of the following qualities: good application and appearance, good stability, and good durability. Good application and appearance refers to one or more of the following properties: flow and leveling, color uniformity, durability of tinted coating to shear, contrast ratio, tint strength, and applied hide. Good durability refers to one or more of the following properties: abrasive scrub resistance as measured by ASTM Test Method D 2486-74A (>400 scrubs), block resistance measured by ASTM-D 4946-89, (>6 after 1 day and 7 days), and adhesion measured by ASTM-D3359 Test Method A (greater than 3A). In some embodiments, the paint, when applied to a surface and dried, has a Gloss at 60° of 5-85 units, for example, over 5 up to 85 units.

The term "quaternary ammonium compounds" as used herein refers to quaternary ammonium salt antibacterial agents having the structural formula:

Formula I

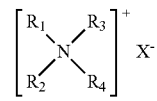

wherein $R_3$ and $R_4$ are linear or branched chain alkyl groups having 1-7 carbons, hydroxyalkyl derivatives of such groups, and mixtures thereof, $R_1$ is a linear or branched chain alkyl group containing 1-20 carbons, a linear or branched chain alkenyl group containing 1-20 carbons, a hydrogen, and mixtures thereof, and $R_2$ is selected from linear or branched chain alkyl groups having 6-20 carbons, a linear or branched chain alkenyl group containing 6-20 carbons, an aryl group, in which the aromatic rings can additionally be substituted, a $C_7$-$C_{18}$ alkylaryl group, in which the aromatic rings can additionally be substituted, benzyl, C1-C18 alkyl benzyl groups, a double bond,

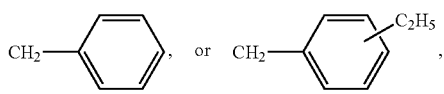

and mixtures thereof, where $R_1$ and $R_2$ may be the same or different from each other, and X represents a halide, a carbonate, a sulfate, a saccharinate, or a carboxylate, in particular chloride, bromide or iodide, propionate, or methosulfate. In some embodiments, a combination of $R_2$, $R_3$ and/or $R_4$ may collective comprise a cyclic moiety. In some embodiments, a combination $R_2$, $R_3$ and/or $R_4$ may collective comprise an aromatic moiety. In some embodiments, the quaternary ammonium compound may be a mixture of compounds according to Formula I. In some particularly useful embodiments the quaternary ammonium compound does not contain or is substantially free of silicon species. Useful examples of quaternary ammonium compounds include, but are not limited to n-alkyl (C8-C18) dimethyl benzyl ammonium chlorides, benzalkonium chloride (where the alkyl side chain is C8, C10, C12, C14, C16 or C18 or mixtures thereof), n-alkyl (C8-C18) dimethyl ethylbenzyl ammonium chlorides, dialkyl dimethyl ammonium chlorides (where the alkyl side chains are C6-C12), didecyl dimethyl ammonium chloride, octyl decyl dimethyl ammonium chloride, dioctyl dimethyl ammonium chloride, octyl-trimethylammonium bromide, decyl-trimethyl-ammonium chloride, lauryl-trimethylammonium chloride, hexadecyl-trimethylammonium chloride, stearyl-trimethylammonium chloride and stearyl-dimethylbenzylammonium chloride, and mixtures of same. A variety of useful quaternary ammonium compounds are commercially available including, but not limited to Barquat®MB-50, Barquat®MB-80, and Bardac® 2250 quaternary ammonium compounds available from Lonza, Inc., BTC®1010, BTC®2125, and BTC®818-80% available from Stepan Company. Other useful quaternary ammonium compounds in accordance with Formula I may include compounds having the following structures:

Formula II

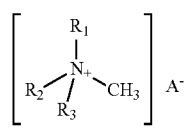

Formula III

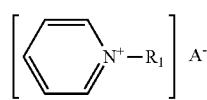

where $R_1$ is a $C_8$-$C_{18}$ alkyl group, a $C_8$-$C_{18}$ alkenyl group, and a hydrogen, where $R_2$ is a double bond, a $C_8$-$C_{18}$ alkyl group, a $C_8$-$C_{15}$ alkenyl group, an aryl group, in which the aromatic rings can additionally be substituted, for example by chlorine and/or bromine, and a $C_7$-$C_{18}$ alkylaryl group, in which the aromatic rings can additionally be substituted, for example by chlorine and/or bromine, where $R_3$ is $C_1$-$C_4$ alkyl group or a $C_1$-$C_4$ hydroxyalkyl, and where A is a halide, a carbonate, a sulfate, a saccharinate, or a carboxylate. For example, A may be a chloride, bromide, acetate, propionate, benzoate or 1 equivalent of sulfate. The radicals $R_1$ and $R_2$ in Formula II can be identical or different. For example, in some embodiments, compounds of Formula II in which $R_1$ and $R_2$ are $C_{10}$-$C_{12}$-alkyl or both radicals $R_1$ and $R_2$ are $C_{10}$-$C_{12}$-alkyl may be used. Compounds of the Formulas II and III are, for example, didecyl-methylhydroxyethylammonium propionate, and lauryl-pyridinium chloride. In some embodiments, the paint may contain a single quaternary ammonium compound, as described above, or mixtures of two or more quaternary ammonium compounds.

In some embodiments, the paint may comprise about 0.25% by weight up to about 3% by weight, for example, about 0.5% to about 1.5% of at least one quaternary ammonium compound. In some embodiments the paint has from about 0.46% to about 0.58% biocidal agent by weight. In some embodiments the paint has from about 0.52 to about 0.56 biocidal agent by weight percentage.

In some embodiments, paint may generally comprise at least about 17%, for example, at least about 17.5% by weight, to about 55% by weight of binder polymer solids. Binders useful in latex paint are known in the art and include polymeric binders, such as acrylics, vinyl acrylics, or styrene acrylics binders. In some embodiments, the paint is formulated to have a binder which is particularly compatible with the quaternary ammonium compound to avoid precipitation. The compatibility of the binder with the quaternary ammonium compound is determined by observing and measuring the degree of precipitation of binder and pigment when the quaternary ammonium compound is added to the paint as described in detail below:

Polymer/Quaternary Ammonium Compound Compatibility Test

Polymer preparation: Selected commercially available and proprietary polymers were diluted to 23.5%/0 weight solids in water.

Quaternary Ammonium compound preparation: Selected commercially available quaternary ammonium compounds were diluted to 50% of their original concentration in water to enhance accurate delivery. (BTC® 2125M-80, BTC® 1210, BTC® 1010 and BTC® 818 quaternary ammonium compounds from Stepan and Barquat® MB-50 and Bardac® 2250 quaternary ammonium compounds from Lonza.

20.0 g of diluted polymer was mixed by hand with sufficient diluted quaternary ammonium compound to yield a concentration of 0.28% active quaternary ammonium compound in the 20.0 g polymer. The mixture was stirred slowly for 5 minutes and allowed to sit at room temperature, covered, for 1 hour. Any liquid was poured off from the vessel. The remaining solids were allowed to dry overnight at 70-77° F. then weighed. A control for each polymer with no quaternary ammonium compound was prepared and the solids weight of the control was subtracted from the weight of the corresponding polymer/quaternary ammonium compound samples in order to account for any losses during handling. The weight of solids observed minus the weight of the control solids results in the compatibility score. The binder polymers tested are listed in Table 1. The quaternary ammonium compounds tested are listed in Table 2. The results of compatibility testing for selected polymer/quaternary ammonium compound pairs is listed in Table 3. The term "compatibility score" for a polymer as used herein refers to the average compatibility score for that polymer with the six quaternary ammonium compounds tested and listed in Table 3.

TABLE 1

| Polymer | Monomer Chemistry | Stabilization Chemistry | Zeta Potential (mV) | pH | Diameter* (nm) |
|---|---|---|---|---|---|
| UCAR™ 6045[1] | Vinyl acrylic | Nonionic | −7.75 | 4.79 | 220 |
| UCAR™ 461[2] | Styrene acrylic | Nonionic | −7.08 | 9.03 | 98.5 |
| ROVACE™ 661[3] | Vinyl acetate/butyl acrylate | Nonionic | −2.6 | 4.33 | 328 |
| JONCRYL® 537[4] | Acrylic | Anionic/Nonionic | −13.14 | 9.08 | 64 |
| JONCRYL® 1530[5] | Acrylic | Anionic/Nonionic | −24.77 | 8.14 | 135 |
| VINNAPAS® EF-811[6] | Vinyl acrylic | Anionic | −20.66 | 4.15 | 214 |
| ACRONAL OPTIVE® 130[7] | Acrylic | Anionic | −14.82 | 7.98 | 162 |
| Proprietary polymer A[8] | Vinyl acrylic | Anionic/Nonionic | −10.1 | 4.76 | 277 |
| Proprietary polymer B[8] | Acrylic | Anionic/Nonionic | −5.49 | 8.79 | 89.6 |
| Proprietary polymer C[8] | Latex acrylic alkyd | Anionic | −20.69 | 7.89 | 111.3 |
| Proprietary polymer D[8] | Styrene-acrylic | Anionic | −13.71 | 8.55 | 93.1 |
| Proprietary polymer E[8] | Styrene-acrylic | Anionic | −21.75 | 8.36 | 89.9 |
| Proprietary polymer F[8] | Styrene-acrylic | Anionic | −7.75 | 4.79 | 220 |
| Proprietary polymer G[8] | Styrene-acrylic | Anionic | −17.26 | 7.98 | 87.4 |
| Proprietary polymer H[8] | Acrylic | Anionic/nonionic | −22 | 7.96 | 153 |
| Proprietary polymer I[8] | Vinyl acrylic | Nonionic | −3.22 | 5.15 | 311 |
| Combination of UCAR™6045/Prop B (75/25) | | Nonionic | −4.3 | 5.15 | |
| Combination of Prop D and Prop E (50/50) | | Anionic | −18.64 | 8.46 | |

*Intensity average diameter measured by a Malvern Zetasizer Nano-S Dynamic Light Scattering Instrument
[1]Available from Arkema, Inc.
[2]Available from Arkema, Inc.
[3]Available from Dow.
[4]Available from BASF.
[5]Available from BASF.
[6]Available from Wacker Chemie.
[7]Available from BASF.
[8]Proprietary polymers made by the assignee of the present application.

TABLE 2

| Quaternary Ammonium Compound Trade Name | Chemical Structure (% Active) |
|---|---|
| BTC®2125 M | n-Alkyl (60% C14, 30% C36, 5% C12, 5% C18) Dimethyl Benzyl Ammonium Chloride (40%) n-Alkyl (68% C12, 32% C14) Dimethyl Ethylbenzyl Ammonium Chloride (40%) |
| BTC® 1210 | Didecyl dimethyl ammonium chloride (48.0%) Alkyl (50% C14, 40% C12, 10% C16) dimethyl benzyl ammonium chloride (32.0%) |
| BARQUAT® MB-50 | Alkyl (C14 50%, C16 10%, C12 40%) Dimethyl Benzyl Ammonium Chloride (50%) |
| BTC® 1010 | Didecyl dimethyl ammonium chloride (80%) |
| BARDAC® 2250 | Didecyl dimethyl ammonium chloride (50%) |
| BTC® 818 | Octyl decyl dimethyl ammonium chloride (80%) |

TABLE 3

| Polymer | BTC2125 M Score (g) | BTC 1210 Score (g) | BARQUAT MB-50 Score (g) | BTC 1010 Score (g) | BARDAC 2250 Score (g) | BTC 818 Score (g) | Average | Standard deviation |
|---|---|---|---|---|---|---|---|---|
| PropI | 0.06 | 0.02 | 0.07 | 0.04 | 0.01 | 0.01 | 0.04 | 0.03 |
| UCAR™ 6045/PropB (75/25) | 0 | 0.05 | 0.04 | 0.1 | 0 | 0.07 | 0.04 | 0.04 |
| PropA | 0.06 | 0.04 | 0.01 | 0 | 0.07 | 0.1 | 0.05 | 0.04 |
| PropB | 0 | 0.04 | 0.05 | 0.11 | 0.04 | 0.08 | 0.05 | 0.04 |
| PropC | 0.12 | 0.05 | 0.03 | 0.04 | 0.08 | 0.03 | 0.06 | 0.04 |
| UCAR™ 6045 | 0.15 | 0.11 | 0.08 | 0.05 | 0.11 | 0.09 | 0.10 | 0.03 |
| Rovace™ 661 | 0.14 | 0.12 | 0.19 | 0.15 | 0.09 | 0.05 | 0.12 | 0.05 |
| PropF | 0.04 | 0.06 | 0 | 0.47 | 0.14 | 0.08 | 0.13 | 0.17 |
| Joucryl® 537 | 0.02 | 0.23 | 0.08 | 0.27 | 0.04 | 0.19 | 0.14 | 0.11 |
| UCAR™ 461 | 0.09 | 0.16 | 0.07 | 0.16 | 0.19 | 0.21 | 0.15 | 0.06 |
| PropD | 0.11 | 0.38 | 0.03 | 0.4 | 0.4 | 0.37 | 0.28 | 0.17 |
| PropE | 0 | 0.27 | 0.08 | 0.51 | 0.64 | 0.31 | 0.30 | 0.24 |
| D/E (50/50) | 0.15 | 0.52 | 0.13 | 0.03 | 0.53 | 0.6 | 0.33 | 0.25 |
| PropG | 0 | 0.38 | 0.34 | 0.34 | 0.5 | 0.51 | 0.35 | 0.19 |
| Joncryl® 1530 | 0.25 | 0.5 | 0.55 | 0.33 | 0.54 | 0.48 | 0.44 | 0.12 |
| Vinnapas® EF811 | 0.97 | 0.23 | 1.52 | 0.42 | 0.36 | 0.72 | 0.70 | 0.48 |

TABLE 3-continued

| Polymer | BTC2125 M Score (g) | BTC 1210 Score (g) | BARQUAT MB-50 Score (g) | BTC 1010 Score (g) | BARDAC 2250 Score (g) | BTC 818 Score (g) | Average | Standard deviation |
|---|---|---|---|---|---|---|---|---|
| PropH | 0.78 | 0.86 | 0.89 | 0.82 | 0.8 | 0.8 | 0.83 | 0.04 |
| Acronal Optive ® 130 | 0.54 | 0.73 | 1.58 | 0.76 | 1.19 | 0.98 | 0.96 | 0.38 |

The compatibility score for each polymer is the average score for the above test for all of the six quaternary ammonium compounds tested. In one embodiment, the polymer has a compatibility score of 0.7 or less. In some particularly useful embodiments, the polymer used in paint has a compatibility score of 0.5 or less. In some embodiments, the polymer used in paint has a compatibility score of 0.35 or less. It should be noted that the average is used as the compatibility score rather than the score for individual polymer/quaternary ammonium compound pairs. It has been determined that for polymers that have an average compatibility score of 0.7 or higher, even if a specific polymer/quaternary ammonium compound pair had an individual score of less than 0.7, that pair was not capable of making a stable composition as defined herein. It has also been determined that for polymers having an average score of 0.5 or less, that a pair having an individual score of above 0.5 were able to make a stable composition.

Prior to paint as disclosed herein, using quaternary ammonium compounds in latex paints was believed detrimental, because the combination results in precipitation, i.e. a less stable composition. In some embodiments, the paint is stable at room temperature for at least one week, for example, at least two weeks, and is also stable at 120° F. for at least one week, for example, at least two weeks. As used herein, a "stable" composition has a change in viscosity of less than 15 Krebs Units ("KU") measured by a Stormer Electronic Viscometer Model KUI+ (sample measured in a pint sized paint can, filled % full and adjusted to 77° F.±1° F.) after 1 week at 120° F. after the addition of a quaternary ammonium compound to the composition. In some embodiments, the paint has a viscosity under 120 KU, for example from 85-120 KU, further for example, about 90-110 OKU as measured by a Stormer Electronic Viscometer Model KUI+.

The results of the stability test are unexpected and surprising considering the zeta potential of the tested polymers. In general the magnitude of the zeta potential is an indicator of the stability of the polymer. Polymer particles with a large (either negative or positive) zeta potential tend to repel each other and are less likely to come together and flocculate or precipitate out of the dispersion. In general, particles with zeta potentials more positive than +30 mV or more negative than −30 mV are considered more stable. Indeed, particles with zeta potentials of −5 mV to +5 mV generally see rapid flocculation with particles having zeta potentials of ±5 mV to ±30 mV being only slightly more stable. In some embodiments, useful polymers include those with zeta potentials between 0 mV and ±30 mV, for example, polymers with zeta potentials between 0 mV and ±25 mV.

The paint may further comprise at least about 10% by weight pigments. Such pigments may comprise inorganic pigments, such as titanium dioxide. The high quality paint comprises, for example, at least about 11% by weight, further for example, at least about 12% by weight, further for example, at least about 13% by weight, further for example, at least about 14% by weight, further for example at least about 15% by weight, further for example, at least about 16%, further for example at least about 17%, further for example, at least about 18%, further for example at least about 19%, and even further for example at least about 20% up to about 30% by weight titanium dioxide. In some embodiments, the high quality paint comprises more than 10% titanium dioxide. Other colored pigments or dyes may also be added to the paint, alone or in combination, to produce a wide range of colored paint. Suitable additional pigments may include calcium carbonate, talc, clay, silicates, aluminum silicates, calcium metasilicates, aluminum potassium silicates, magnesium silicates, barium sulfates, nepheline syenite, feldspar, zinc oxides or sulfides, or others known to those skilled in the art. Such additional colored pigments may be included in amounts up to about 30% by weight, for example, about 10% to about 20%. In some cases, "pigments" may also refer to functional fillers which are non-water soluble solids. Such functional fillers may include solids which provide additional functional characteristics to the paint, for example, intumescent ingredients, such as ammonium polyphosphates, melamines, pentaerythritol and similar compounds. In some embodiments, the paint is substantially free or totally free of intumescent ingredients such as ammonium polyphosphates, melamines, and pentaerythritol and similar compounds.

The pigment volume concentration, or PVC, of a coating provided by a paint is the ratio of the volume of pigments (including functional fillers) to the volume of total non-volatile material (i.e. pigment and binder) present in the coating. In some embodiments the paint may provide a surface comprising a coating preferably having a PVC of about 5 to about 60. In addition, the paint has a maximum solids content of less than 65% by weight, for example, about 25% by weight to about 60% by weight, further for example about 30% by weight to about 58% by weight.

In some embodiments the paint may also include various other additives, including but not limited to thickeners, such as urethane thickeners, and acrylic thickeners in amounts up to about 10% by weight, for example about 1% to about 2%. Synthetic organic materials might also be incorporated; these include plastic beads, hollow spheres or other similar materials. Other optional components include glycols such as ethylene and/or propylene glycol in amounts up to about 7% and other solvents such as diethylene glycol dibenzoate and dipropylene glycol dibenzoate in amounts up to about 3%. The paint may also contain pigment dispersing agents which can be solvents or surfactants; wet paint preservatives; dry film preservatives; foam control agents such as oils, fatty acids and silicones; slip and mar additives; adhesion promoters, and/or other known paint additives.

In some embodiments, the paint may also comprise other biocides including but not limited to metal ion containing compounds, polymeric biocides, heterocyclic compounds, phenols, organometallics, aldehydes, proteins, peroxygens, alcohols, enzymes, polypeptides, and halogen releasing compounds.

In some embodiments, paints are generally formulated to have a pH between 7 and 10.

It has been observed that by premixing the quaternary ammonium compounds with a mixture of ester alcohols and oleic acid monoester propylene glycols that higher concentrations of quaternary ammonium salts can be achieved. This method comprises mixing together quaternary ammonium compound, with an ester alcohol, such as Texanol™ solvent, and oleic acid monoester propylene glycol, such as Loxanol® EFC, and then adding the mixture to the paint. In some embodiments, the ester alcohol and oleic acid monoester propylene glycol are functional components of the paint. In some embodiments the ester alcohol and oleic acid monoester propylene glycol are added to the paint only by this method. In some embodiments, portions of the normally used amounts of the ester alcohol and oleic acid monoester propylene glycol are used to prepare the premix. For example, in some embodiments, about half of the normally used amounts of the ester alcohol and oleic acid monoester propylene glycol may be mixed with the quaternary ammonium compound for addition to the paint.

In some embodiments, the quaternary ammonium compound included in the paint may be encapsulated within a solid shell ("microcapsule") material. Microencapsulation of the quaternary ammonium compound serves to protect the paint from flocculation by minimizing or eliminating direct interactions between the quaternary ammonium compounds and the latex binder and other paint ingredients. In one embodiment, the microcapsule completely isolates the quaternary ammonium compound from interaction with the other paint components. The microcapsule may have a structure which allows it to isolate the quaternary ammonium compound from the rest of the paint components, but opens or bursts upon drying of the paint film to allow the quaternary ammonium compound to contact and kill or inactivate microorganisms or viruses which come into contact with the surface of the coating comprising dried paint film. For example, the capsule could be designed to open as the pH of the system changes as the paint dries. In some embodiments, the evaporation of water from the system could cause the capsule to desiccate and burst. Means for encapsulating active materials (also referred to as delivery systems) are known to those of ordinary skill in the art. Any such methods which are known or are later developed may be used.

It should be noted that in order to make a latex paint, an appropriate dispersant/surfactant system is needed in order to disperse the pigments in the paint. The process for selecting dispersants/surfactants for paint is well known to those of ordinary skill in the paint formulation art. After selecting a compatible polymer and quaternary ammonium compound as described herein, one of ordinary skill in the art would be able to select a dispersant/surfactant combination in order to make a desired paint.

In one useful embodiment, the dried paint film provides a coating that is capable of reducing gram positive bacteria, gram negative bacteria, and viruses by greater than 3 logs within 2 hours of application. The bacterial and viral reduction is measured in a test based on the JIS Z 2801 modified for paints as described herein and compared to a control paint that does not contain a quaternary ammonium compound.

EXAMPLES

Exemplary stable, high quality paint were made by mixing the following components using techniques known to those of ordinary skill in the art:

Comparative Example

| COMPONENT | Weight % |
|---|---|
| UCAR ™ 6045 | 30.62 |
| Proprietary Polymer B (55% solids) | 8.19 |
| Defoamer[1] | 0.25 |
| WATER | 19.73 |
| Hydroxyethyl cellulose thickener[2] | 0.02 |
| Dispersant[3] | 0.49 |
| Titanium Dioxide (dry) | 23.29 |
| Pigment[4] | 9.05 |
| Pigment[5] | 3.45 |
| Coalescent[6] | 0.26 |
| Rheology modifier[7] | 2.85 |
| Rheology modifier[8] | 1.29 |
| Nonionic surfactant[9] | 0.43 |
| Aqueous ammonia | 0.08 |
| Total | 100 |

[1]BYK ® 024 from Byk Chemie
[2]CELLOSIZE ™ QP-4400H from Dow
[3]TAMOL ™ 1254 from Dow.
[4]MINEX ™ 4 from Unimin Specialty Minerals
[5]MINEX ™ 2 from Unimin Specialty Minerals
[6]LOXANOL ™ EFC 100 from Cognis
[7]ACRYSOL ™ RM-8W from Dow
[8]ACRYSOL ™ RM-2020 NPR from Dow
[9]TRITON ™ X-102 from Dow Example 1 was made by adding 0.65 g of Barquat MB-80 Quaternary Ammonium Compound to a paint prepared in accordance with the Comparative Example then stirring with an air mixer at room temperature for 10 minutes.

Paint as described herein were tested for antimicrobial activity. Paint coupons for the bacterial testing were made using the following procedure: A 7 mil wet film caster was used to draw down HARMONY® interior acrylic latex (flat, extra white) paint on a black Leneta scrub chart P121-10N. The base coat was air dried overnight and a 7 mil film caster was then used to draw down the paint of Example 1 over it. After air drying overnight, a second 7 mil coating of Example 1 was applied and allowed to air dry overnight. A control with a base coat of Harmony® interior acrylic latex paint and two coats of the Comparative Example paint was made using the same process. An additional control sample consisting of unpainted Leneta chart was tested in the same manner as the paint samples.

To test the ability of a coating provided by the paint to kill bacteria, Japanese Industrial Standard JIS Z 2801 was used with the following adaptations: The *E. coli* ATCC 11229 was used instead of ATCC8739 and 0.3 ml organic soil load (25 mL Fetal Bovine Serum, VWR Research Grade, Catalog #97068-066+5 mL Triton X-100, Sigma Aldrich Laboratory Grade, Catalog #X100-100ML) was added to the culture. Three 1 in ×1 in pieces of Parafilm laboratory film were placed in a sterile glass Petri dish and a 20 cm×20 cm sample from the center of the paint drawdown was placed on each of the prepared coupons. Twenty-five μl of inoculum were placed on the paint surface. After inoculation, the samples were covered with a glass coverslip and incubated for 2 hours at saturation humidity. The Comparative Example paint was processed in the same way as the paint of Example 1. The bacteria was recovered by placing the paint square, parafilm and coverslip in a sterile 50 ml conical tube filled with 5 ml of phosphate buffered saline (PBS) and vortexed for 15-30 seconds to release the remaining bacteria back into solution. A total viable count (TVC) was performed on the eluent solution. Colony Forming Units/milliliter (CFU/ml) of bacteria recovered from each sample was calculated, and results were reported as the log reduction in CFU/ml of the antimicrobial paint compared to the untreated paint. A measurement of the CFU/ml of the inoculum was made by transferring 25 µl bacterial culture directly into a sterile 50 ml tube containing 5 ml of PBS, and completing the test method. The CFU/ml of the Staph innoculum was determined to be $9.7 \times 10^5$ and the CFU/ml of the E. Coli innoculum was determined to be $1.0 \times 10^6$. The effectiveness of the test conditions was judged to be adequate because the CFU/ml of the innoculum was between $2.5 \times 10^5$ and $1 \times 10^7$ CFU/ml and the CFU/ml of the unpainted Leneta chart and parafilm control and the comparative example were between 5 and 6.7 $Log_{10}$ CFU/ml.

The results of the antimicrobial testing for coatings provided by these paint are summarized in Table 4.

TABLE 4

| Sample | $Log_{10}$ CFU/ml, S. aureus 2 hrs | $Log_{10}$ CFU/ml, E. coli 2 hrs |
|---|---|---|
| Unpainted Control | 5.6 | 5.9 |
| Comparative Example: | 5.5 | 5.3 |
| Example 1: | 1.2 | 1.3 |
| Log reduction | 4.4 | 4.6 |

Separate paint coupons for viral testing were made using the same procedure as described above for the bacterial testing except that no unpainted films were used. To test the coating's ability to inactivate viruses, the following procedure was used. A Stock Influenza A virus (ATCC VR-544 Strain Hong Kong) in Minimum Essential Medium, containing 1% fetal bovine serum was used in this test. The stock virus was stored at ≤−70° C. On the day of testing, the stock virus was titred by 10-fold serial dilutions and assayed for infectivity to determine the starting titer of the virus. The starting titer for the test was $1 \times 10^{7.75}$ $TCID_{50\%}$ (Tissue Culture Infective Dose)/0.10 ml.

Replicate 1 in ×1 in coupons having coatings provided by the paint of the Comparative Example and Example 1 were placed in sterile Petri dishes. The coupons were irradiated with UV light for about 15 minutes on each side. The samples were inoculated with a 1001 µl aliquot of the test virus. The inoculum was covered with carrier film (20 mm×20 mm prepared from a sterile stomacher bag) and the carrier film was pressed down so that the test virus spread over the film but did not spill over the edge of the film. The exposure time began when each sample was inoculated. The samples were transferred to a controlled chamber set at 20° C. in a relative humidity of 40% for the duration of the exposure times. The coupons were kept in contact with the virus for 1 or 2 hours at 20° C. and 40% relative humidity.

Following each exposure time, a 1.00 ml aliquot of test medium (Minimum Essential Medium supplemented with 1% v/v heat inactivated fetal bovine serum, 10 micrograms/ml gentamycin, 10 units/ml penicillin, and 2.5 micrograms/ml amphtericin B) was individually pipetted onto each test and control paint coupons as well as to the underside of the film used to cover each sample. The surface of each paint coupon was scraped with a sterile plastic cell scraper. The test medium was collected, mixed using a vortex type mixer and serial 10-fold dilutions were prepared. The serial dilutions were assayed for infectivity on Rhesus monkey kidney cells. The geometric mean of two $TCID_{50\%}$/0.1 ml replicates for each of the Comparative Example and Example 1 was determined and the log reductions at each contact time were calculated by subtracting the result of Example 1 from the Comparative Example.

The results of the viral testing for coatings provided by paint are summarized in Table 5

TABLE 5

| Sample | Mean $TCID_{50\%}$/0.1 ml (Tissue Culture Infective Dose) at 1 hour | Mean $TCID_{50\%}$/0.1 ml (Tissue Culture Infective Dose) at 2 hours |
|---|---|---|
| Comparative Example: | 7.63 $Log_{10}$ | 7.38 $Log_{10}$ |
| Example 1: | ≤1.5 $Log_{10}$ | ≤1.5 $Log_{10}$ |
| Log reduction | ≥6.13 | ≥5.88 |

Assessing Self-Sustaining Biocidal Activity

Self-sustaining means that the surface (whether inherently, or through the use of a coating) provides biocidal effects and does not need any sort of "recharging" or replenishment. One effective way of measuring the efficacy at which a surface provides a self-sustaining biocidal effect is to calculate that surface's Rook Rating. The Rook Rating provides a relative comparison of initial efficacy of the biocidal activity of a surface and efficacy of the biocidal activity of the surface after some elapsed period of time.

Rook Rating$_{Time\ Period}$=Efficacy$_{Time\ Period}$/Efficacy$_{Initial}$

The Rook Rating may also provide a relative comparison of initial efficacy of the biocidal activity of a surface and efficacy of the biocidal activity of the surface after an event or series of event has occurred.

Rook Rating$_{Event}$=Efficacy$_{Event}$/Efficacy$_{Initial}$

Without wishing to be limited by theory, it is estimated that a wall that is being used commercially will be cleaned with an institutional cleaner, about once a month. Accordingly, over a four year (48 month) time period a surface on that wall will be washed 48 times. Additional washings, however, may be necessary over that time period. As such over a four years (48 month) time period a surface on the wall may be washed 50 times. Accordingly, the Rook Rating of a coating after 50 washings may be indicative of the Rook Rating of the coating for a four year (48 month) time period.

The Rook Rating for bacteria for a four years (48 month) time period is greater than about 0.90. In some embodiments, the Rook Rating for bacteria a four years (48 month) time period is greater than 0.99. In other embodiments, the Rook Rating for bacteria a four years (48 month) time period is greater than 0.999. In other embodiments still, the Rook Rating for bacteria a four years (48 month) time period is greater than 0.9999. The bacteria may be selected from the group consisting of: gram positive, gram negative, pathogenic, disease-causing, methicillin-resistant *Staphylococcus aureus*, *Staphylococcus aureus*, vancomycin-resistant *Enterococcus faecalis*, *Escherichia coli*, *Enterobacter aerogenes*, and combinations thereof.

Initial Biocidal Efficacy Testing

The initial biocidal efficacy may be measured by determining the level of biocidal activity on a surface shortly after exposure to bacteria, viruses, or other microbes. For initial efficacy, a 48 hour culture of *E. coli* is supplemented with fetal bovine serum (5% final concentration) and Triton X-100 (0.01% final concentration). Sterilized surfaces, which are coated with the Biocidal Paint containing a biocidal agent and the Control Paint lacking an identified biocidal agent, are inoculated with 40 µL of the bacterial culture and supplemented with the fetal bovine serum. After 120 minutes of exposure at 25° C. and 60% relative humidity, treated surfaces are transferred aseptically to 20 mL of neutralizer medium (Criterion™ Letheen Broth by Hardy Diagnostics, VWR Catalog #89405-582), and sonicated for five minutes to remove bacteria attached to the surface. Serial dilutions of the neutralized surfaces are then plated in duplicate onto recovery medium (Becton Dickenson Tryptic Soy Agar, VWR Catalog #90000-050 with 5% defibrinated whole sheep blood, Innovative Research Inc., VWR Catalog #102768-564) using standard spread plate technique to determine the TVC. The agar plates are incubated for 48 hours at 35-37° C. to allow for colony formation. Colony enumeration is performed immediately following the incubation period. Resulting colonies are counted and used to calculate the biocidal efficacy of the coatings. The test organisms, or bacteria, may be Escherichia coli O157:H7 (("E. coli") (American Type Culture Collection #35150), Vancomycin-Resistant Enterococcus faecalis ("VRE") (American Type Culture Collection #51575), Enterobacter aerogenes ("EA") (American Type Culture Collection #13048), Staphylococcus aureus ("SA") (American Type Culture Collection #6538), Methicillin Resistant Staphylococcus aureus ("MRSA") (American Type Culture Collection #33592).

Washing of the Coating to Simulate Extended Use

A washing may simulated by coating a scrub chart panel with a paint and subjecting coated scrub chart panel to wear cycle in the following manner.

A commercially available cleaner (Best Yet Citrus Cleaner™—Boyd Enterprises, Granville, Tex.) is prepared according to the manufacturer's recommended dilution ratio of 59.14 mL of detergent per 3726 mL of cold tap water. A cellulose sponge is soaked and then wrung to remove excess liquid. The sponge is then attached to a tester tray for testing scrubbing on top of the painted scrub chart. (Gardco Washability Tester Tray—Paul N. Gardner Company, Inc., Pompano Beach, Fla.). The Gardco Washability Tester Tray (Model D10, Paul N. Gardner Company, Inc., Pompano Beach, Fla.) was set to two, and two cycles are performed on a scrub chart to simulate one complete wear cycle which is the equivalent to four washes, or one month of cleaning. After each wear cycle, the sponge and scrub chart panel are removed from the Gardco Washability Tester Tray. The sponge is placed in the cleaning solution and allowed to absorb fresh liquid, while the washed scrub chart panel is allowed to dry in a horizontal position at room temperature for at least ten minutes. Panels are visually confirmed to be dry prior to further wear cycles being initiated. Panels and sponges are then re-attached to the Gardco Washability Tester Tray as described earlier and the wear cycle is repeated as many times as desired.

As each wear cycle is equivalent to one washing, and 50 washing would occur over a four year (48 month) period of time, a total of 50 wear cycles would be equivalent to a four year (48 month) period of time. Thus the biocidal efficacy of the surface after 50 wear cycles would be equivalent to the biocidal efficacy of the surface after four year (48 months).

The biocidal efficacy a scrub chart panel after one or more wear cycles can be determined by cutting the panel into 1"×1" carrier squares. The panel squares may then be innoculated with 40 µL of a bacterial culture and supplemented with the fetal bovine serum. After a sufficient exposure time, surfaces may be aseptically transferred to 20 mL of neutralizer medium (Criterion™ Letheen Broth by Hardy Diagnostics, VWR Catalog #89405-582) and sonicated for five minutes to remove bacteria attached to the panel surface. Serial dilutions of the neutralized panels may then plated in duplicate onto recovery medium (Becton Dickenson Tryptic Soy Agar, VWR Catalog #90000-050 with 5% defibrinated whole sheep blood, Innovative Research Inc., VWR Catalog #102768-564) using standard spread plate technique to determine TVC. The agar plates may then be incubated for 48 hours at 35-37° C. to allow for colony formation. Colony enumeration may be performed immediately following the incubation period. Resulting colonies may be counted and used to calculate the biocidal efficacy of the panel. The test organisms, or bacteria, may be Escherichia coli O157:H7 (("E. coli") (American Type Culture Collection #35150), Vancomycin-Resistant Enterococcus faecalis ("VRE") (American Type Culture Collection #51575), Enterobacter aerogenes ("EA") (American Type Culture Collection #13048), Staphylococcus aureus ("SA") (American Type Culture Collection #6538), Methicillin Resistant Staphylococcus aureus ("MRSA") (American Type Culture Collection #33592).

Percent Reduction Calculation

The average number of surviving organisms per panel may be determined by the following calculation:

$$CFU/\text{Carrier} = \frac{(\text{average number of colonies/panel@dilution}) \times (\text{dilution factor}) \times (\text{volume neutralizer solution})}{(\text{volume plated})}$$

The carrier population may calculated using the data from recovery plates with less than 250 colony forming units per plate, and ideally with colony forming units between 25-250 colony forming units per plate.

The geometric mean of the number of surviving organisms on the panel may be determined by the following calculation:

$$\text{Geometric Mean} = \frac{\text{Antilog of } \log_{10}X_1 + \log_{10}X_2 + \ldots \log_{10}X_N}{N}$$

Where X equals CFU/panel and N equals the number of replicates tested

What is claimed is:

1. A surface comprising:
   (a) a coating, the coating having a dry coating thickness of about 25 microns to about 400 microns, and wherein the coating is a dried film of a liquid paint, said liquid paint having a pigment volume concentration (PVC) of less than about 60 and comprising:
      (i) a biocidal agent comprising a quaternary ammonium compound;
      (ii) at least about 10% by weight pigment;
      (iii) a binder polymer having a compatibility score of 0.5 or less, and
   (b) wherein the surface has the ability to kill bacteria, the bacteria selected from the group consisting of: gram positive, gram negative, pathogenic, disease-causing, methicillin-resistant Staphylococcus aureus, Staphylococcus aureus, vancomycin-resistant Enterococcus faecalis, Escherichia coli, Enterobacter aerogenes, and combinations thereof, characterized by a Rook Rating for said bacteria of greater than 0.90, the Rook Rating being calculated from the following formula:

$$\text{Rook Rating} = \text{Efficacy}_{Event}/\text{Efficacy}_{Initial}$$

the Efficacy$_{Initial}$ being the initial biocidal efficacy of a test surface coated with the coating and the Efficacy$_{Event}$ being the biocidal efficacy of the test surface after fifty washings.

2. The surface according to claim 1 wherein the Rook Rating for said bacteria is greater than 0.99.

3. The surface according to claim 2 wherein the Rook Rating for said bacteria is greater than 0.999.

4. The surface according to claim 3 wherein the Rook Rating for said bacteria is greater than 0.9999.

5. The surface of claim 1, wherein the quaternary ammonium compound has the structural formula:

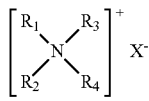

wherein $R_1$ and $R_2$ are linear or branched chain alkyl groups or mixtures of groups having 1-7 carbons, $R_3$ is a linear or branched chain alkyl group or a mixture of groups containing 6-20 carbons, and $R_4$ is a linear or branched chain alkyl-group or a mixture of groups having 6-20 carbons, benzyl or alkyl benzyl groups, or

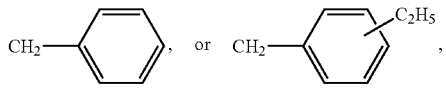

where $R_3$ and $R_4$ may be the same or different from each other, and X represents a halide, carbonate, methosulfate, or saccharinate.

6. The surface according to claim 5, wherein the paint comprises about 0.46 to about 0.58 percent by weight of the quaternary ammonium compound.

7. The surface of claim 5, wherein the paint comprises about 0.25% to about 3% by weight of the quaternary ammonium compound.

8. The surface of claim 5, wherein the paint comprises about 0.5% to about 1.5% by weight of the quaternary ammonium compound.

9. The surface according to claim 1, wherein the liquid paint further comprises at least about 55% by weight solids and wherein the coating has dry coating thickness of at least about 167.6 microns.

10. The surface of claim 5, wherein the quaternary ammonium compound is substantially free of silicon.

11. The surface of claim 1, wherein the quaternary ammonium compound has the structural formula:

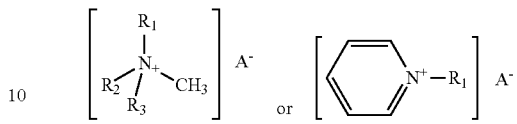

where $R_1$ is $C_8$-$C_{18}$ -alkenyl or -alkenyl, where $R^2$ is $C_8$-$C_{18}$ -alkyl or -alkenyl, aryl or $C_7$-$C_{18}$ -aralkyl, in which aromatic rings can additionally be substituted, where $R_3$ is $C_1$-$C_4$-alkyl, where $R_4$ is H or methyl, and where A is chloride, bromide, acetate, propionate, benzoate or sulfate.

12. The surface of claim 1, wherein the biocidal agent comprises one or more of from n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$alkyl, dialkyl dimethyl ammonium chlorides, the alkyl side chain being $C_6$-$C_{12}$, n-alkyl dimethyl benzyl ammonium chloride, and dodecyl dimethyl ammonium chloride, octyl decyl dimethyl ammonium chloride, dioctyl dimethyl ammonium chloride, didecyl dimethyl ammonium chloride, or mixtures thereof.

13. The surface according to claim 1, wherein the liquid paint further comprises at least about 15% by weight solids and wherein the coating has dry coating thickness of about 5.7 microns to about 66 microns.

14. The surface according to claim 1, wherein the liquid paint further comprises at least about 35% by weight solids and wherein the coating has dry coating thickness of about 35.5 microns to about 101.6 microns.

15. The surface according to claim 1, wherein the coating has a viscosity of under 120 KU.

* * * * *